(12) United States Patent
Orfield et al.

(10) Patent No.: US 11,235,201 B2
(45) Date of Patent: Feb. 1, 2022

(54) WEIGHT MACHINE SENSOR

(71) Applicant: ShapeLog, Inc., Ann Arbor, MI (US)

(72) Inventors: Nolan Orfield, Ann Arbor, MI (US); Brandon Hazelton, Ann Arbor, MI (US); Jesse J Raleigh, Grand Rapids, MI (US); Andrew Stephen Muth, Evanston, IL (US)

(73) Assignee: ShapeLog, Inc., Ann Arbor, MI (US)

( * ) Notice: Subject to any disclaimer, the term of this patent is extended or adjusted under 35 U.S.C. 154(b) by 404 days.

(21) Appl. No.: 15/997,200

(22) Filed: Jun. 4, 2018

(65) Prior Publication Data

US 2018/0345080 A1    Dec. 6, 2018

Related U.S. Application Data

(60) Provisional application No. 62/514,941, filed on Jun. 4, 2017.

(51) Int. Cl.
*A63B 24/00*    (2006.01)
*A63B 21/062*   (2006.01)
(Continued)

(52) U.S. Cl.
CPC .......... *A63B 24/0062* (2013.01); *A61B 5/224* (2013.01); *A63B 21/0628* (2015.10); *A63B 24/0075* (2013.01); *A63B 71/0622* (2013.01); *A61B 5/1176* (2013.01); *A61B 2503/10* (2013.01); *A63B 2024/0065* (2013.01); *A63B 2220/51* (2013.01); *A63B 2220/805* (2013.01);
(Continued)

(58) Field of Classification Search
CPC ............ A63B 24/0062; A63B 21/0628; A63B 24/0075; A63B 71/0622; A63B 2225/15; A63B 2225/54; A63B 2220/51; A63B 2220/89; A63B 2230/75; A63B 2225/52; A63B 2024/0065; A63B 2225/20; A63B 2220/833; A63B 2220/805; A63B 2220/807; A61B 5/224; A61B 2503/10; A61B 5/1176

See application file for complete search history.

(56) References Cited

U.S. PATENT DOCUMENTS 4,919,418 A * 4/1990 Miller ................... A63B 21/151
                                                482/112
5,151,071 A * 9/1992 Jain ....................... A63B 21/154
                                                482/101
(Continued)

FOREIGN PATENT DOCUMENTS

CN            201464091 U     5/2010

*Primary Examiner* — Sundhara M Ganesan
(74) *Attorney, Agent, or Firm* — Stephen J. Kontos; Veln PLLC (57) ABSTRACT

A weight machine sensor includes a force sensor, a position sensor, and a processor. The force sensor is programmed to output a force signal representing a force applied to a pulley-disposed on a cable incorporated into exercise equipment having a stack of weights. The position sensor is programmed to detect motion of the stack of weights and output a position signal representing the motion detected. The processor is programmed to receive the force signal and the rotation signal and determine, from the force signal and the position signal, exercise data including an amount of exercise resistance and a number of repetitions performed.

20 Claims, 8 Drawing Sheets

(51) Int. Cl.
*A63B 71/06* (2006.01)
*A61B 5/22* (2006.01)
*A61B 5/1171* (2016.01)

(52) U.S. Cl.
CPC ... *A63B 2220/807* (2013.01); *A63B 2220/833* (2013.01); *A63B 2220/89* (2013.01); *A63B 2225/15* (2013.01); *A63B 2225/20* (2013.01); *A63B 2225/52* (2013.01); *A63B 2225/54* (2013.01); *A63B 2230/75* (2013.01)

(56) References Cited

U.S. PATENT DOCUMENTS

| | | | | |
|---|---|---|---|---|
| 5,655,997 | A * | 8/1997 | Greenberg | A63B 21/063 482/1 |
| 6,358,188 | B1 * | 3/2002 | Ben-Yehuda | A63B 24/00 482/8 |
| 8,069,737 | B2 | 12/2011 | Hanoun | |
| 9,409,053 | B1 * | 8/2016 | Todd | G16H 40/67 |
| 9,814,920 | B1 * | 11/2017 | Monterrey | A63B 21/4035 |
| 2004/0176226 | A1 * | 9/2004 | Carlson | A63B 21/00076 482/112 |
| 2006/0293151 | A1 * | 12/2006 | Rast | A63B 21/0023 482/8 |
| 2007/0213183 | A1 * | 9/2007 | Menektchiev | A63B 24/00 482/94 |
| 2008/0248926 | A1 * | 10/2008 | Cole | A63B 21/0628 482/5 |
| 2009/0013804 | A1 * | 1/2009 | Hanoun | G01L 5/102 73/862.474 |
| 2010/0197462 | A1 * | 8/2010 | Piane, Jr. | A61B 5/22 482/5 |
| 2010/0240493 | A1 * | 9/2010 | Wang | A63B 21/0628 482/4 |
| 2011/0224046 | A1 * | 9/2011 | Chen | A63B 21/154 482/8 |
| 2012/0004076 | A1 * | 1/2012 | Fenster | A63B 21/0628 482/8 |
| 2012/0094804 | A1 * | 4/2012 | Bell | A63B 21/0083 482/8 |
| 2012/0220428 | A1 * | 8/2012 | Carlson | A63B 21/156 482/8 |
| 2013/0310221 | A1 * | 11/2013 | Zuber | G06F 19/3481 482/8 |
| 2015/0209609 | A1 * | 7/2015 | Oteman | A63B 71/0686 482/8 |
| 2015/0335950 | A1 * | 11/2015 | Eder | G06Q 10/06314 482/8 |
| 2016/0166460 | A1 * | 6/2016 | Murphy | A63B 21/0004 601/34 |
| 2016/0199697 | A1 * | 7/2016 | Orfield | A63B 21/0628 482/8 |
| 2017/0157489 | A1 * | 6/2017 | Young | A63B 21/4047 |
| 2017/0282013 | A1 * | 10/2017 | Paulsen | A63B 23/03525 |
| 2018/0099184 | A1 | 4/2018 | Eder | |
| 2018/0243599 | A1 * | 8/2018 | Lacey | A63B 21/156 |
| 2018/0326242 | A1 * | 11/2018 | Jaquish | A63B 21/00069 |
| 2018/0345080 | A1 * | 12/2018 | Orfield | A63B 24/0075 |
| 2019/0033148 | A1 * | 1/2019 | Goodstadt | A63B 21/0628 |

* cited by examiner

WEIGHT MACHINE SENSOR

CROSS-REFERENCE TO RELATED APPLICATIONS

This application claims priority to provisional patent application No. 62/514,941 titled "SENSOR EQUIPPED EXERCISE MACHINE PULLEY" filed on Jun. 4, 2017, the contents of which are hereby incorporated by reference in their entirety.

BACKGROUND

The advent of fitness trackers coupled with the increasing ease with which digital data can be wirelessly recorded has led to a proliferation of technologies that allow users to track and gain insights from their exercise activities.

DETAILED DESCRIPTION

Despite the increased interest in digitizing and recording users' fitness activity, currently-available products do not accurately capture the activity performed on weight machines commonly found in home gyms, commercial gyms, corporate wellness facilities, or physical therapy centers. Thus, a device which can integrate this significant aspect of physical fitness into the expanding ecosystem of fitness trackers would be beneficial.

Weight machines typically allow users to set his/her training resistance by isolating some fraction of a stack of weights using a pin, lever, or some other mechanism. The mechanical configuration of the machine is such that when the user moves in the intended fashion the weights that were isolated move in accordance with the movement of the body, thereby providing resistance to the desired muscle group or groups that is proportional to the weight setting selected by the user. Translating motion of the body into the rising and falling of the weight stack is achieved by using a cable or belt and a series of one or more pulleys to redirect the tension such that it resists the movement. Using a stack of weights is the most common form of resistance for these machines, sometimes referred to as "selectorized" machines, but resistance can be provided in other ways. For example, resistance can be provided by flexing one or more beams, or by an electromechanical device such as a motor or dynamo.

One solution for recording fitness activity on an exercise machine involves a weight machine sensor that can detect repetitions performed on the exercise machine, especially one that requires a user to tension a cable to provide resistance. An example of this sensor is a device that can detect the weight lifted—or force exerted—by the user and the number of repetitions performed on the exercise equipment. The device includes a force sensor programmed to output a force signal representing a force applied to a cable associated with the piece of exercise equipment. The weight machine sensor further includes a rotation sensor to determine from the rotation of the pulley, providing information about the exercise being performed. Rotation of the pulley can be used to measure the physical movement of the stack of weights, but alternatively a position sensor or rangefinder can also be used to achieve the same result. The weight machine sensor further includes a processor programmed to receive the force signal and rotation signals and determine, from these signals, exercise data including an amount of weight lifted and a number of repetitions performed.

The exercise data can be transmitted to and viewed by the user of the exercise equipment. In some instances, the exercise data may be transmitted to a remote server. The user can view the exercise data by accessing the data stored on the remote server via, e.g., a computer such as a smartphone, tablet computer, a desktop computer, a laptop computer, or the like.

The elements shown may take many different forms and include multiple and/or alternate components and facilities. The example components illustrated are not intended to be limiting. Indeed, additional or alternative components and/or implementations may be used. Further, the elements shown are not necessarily drawn to scale unless explicitly stated as such.

Figure 1:
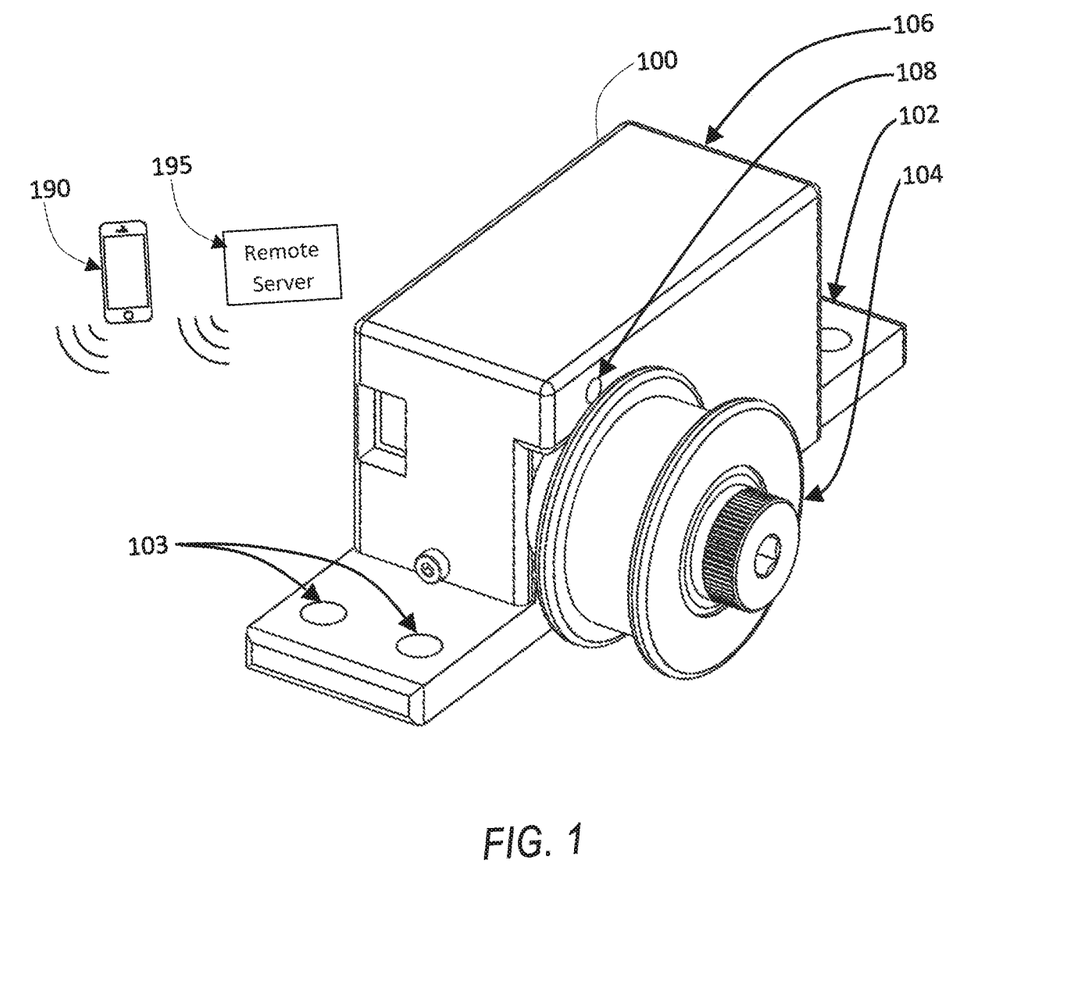
FIG. 1 shows a configuration of the weight machine sensor that can be attached to a variety of weight machines.

FIG. 1 shows one basic form of the weight machine sensor 100 which features a base 102, a pulley 104, and a cover 106 to protect the enclosed electronic components. In this implementation, a rotation sensor 108 extends through the cover 106 to measure rotation of the pulley 104 as a way to calculate exercise data. Rotation data can be translated into position data for the weight stack 134 and therefore also velocity of the weight stack 134, range of motion, and repetitions. When this position or rotation signal is combined with information about the tension in the cable other metrics such as work output, power output, and calories burned can also be calculated. The rotation sensor 108 shown in the figure is an optical sensor that interacts with features or marks on the pulley 104 to infer information about the amount of rotation and direction of rotation of the pulley 104.

Some rotation sensors, or rotary encoders, work by reflecting light off of a surface and observing the pattern of reflected light, while others feature a light emitting source opposed from a light detector that observes the pattern of light passed through a series of slots, protrusions, or other feature on a rotating wheel. This rotation sensor might also feature multiple sensors that, when used simultaneously, can help determine the direction of rotation from the pattern observed when comparing the two signals. Magnets can also be embedded in the pulley or other rotating feature allowing for hall effect or reed sensors to determine rotation information from the resulting magnetic interaction signal. Optical or magnetic rotation sensors do not require direct physical contact with the pulley and therefore do not cause friction nor will they wear out mechanically. These are examples of incremental rotation sensors that only measure the relative change in angular position. A potentiometer or other absolute position sensor could also be used because the pulley 104 is limited to a specific number of revolutions depending upon the diameter of the pulley and range of travel of the weight stack 134.

The weight machine sensor 100 shown in FIG. 1 is modular in nature such that it can be placed at various locations and on various makes and models of weight machines without significant re-engineering. The compactness of the device and simple hole-mounts 103 featured in the base 102 serve to make the sensor more universally implementable with some simple additional mounting brackets, shims, and/or fasteners. The device could therefore be used to retrofit existing lines of equipment or could be directly integrated into the machines as they are being manufactured.

Figure 2:
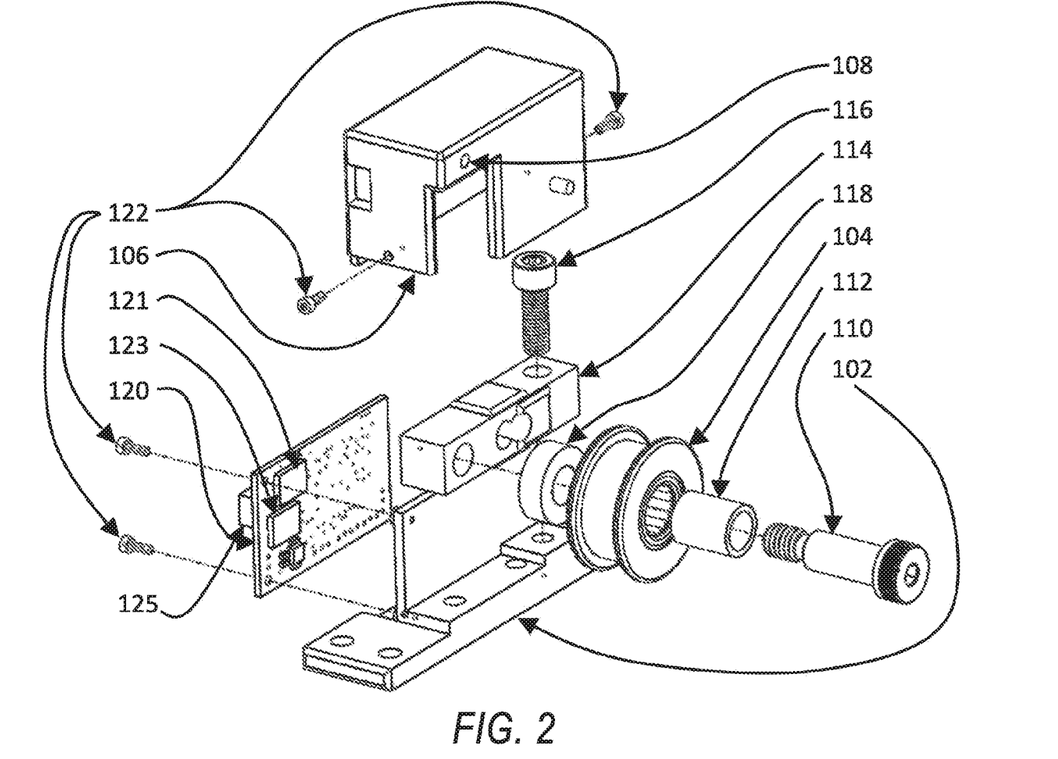
FIG. 2 illustrates an exploded view of the device shown in FIG. 1.

FIG. 2 shows an exploded view of the example device shown in FIG. 1 with the cover 106 removed to reveal some of the internal components. Removal of the screws 122 allows for accessing or servicing the internal components. A shoulder bolt 110 connects the pulley 104 to a force sensor 114 with a bushing 112 utilized to fill the difference between the inner diameter of the bearing in the pulley 104 and the outer diameter of the shoulder bolt 110. The force sensor is then rigidly fixed to the base 102 with a bolt 116. The example force sensor 114 shown here features a strain gauge (e.g., a metal foil gauge) fixed directly to a rigid beam that is deflected when a load is applied. Since the force sensor features a cantilevered body designed to deflect an amount proportional to the force applied, the force may be measured by the strain gauge, which may include a metallic foil with an electrical resistance that changes based on the amount of deflection. The change in resistance may be amplified via, e.g., a Wheatstone bridge circuit or other type of amplification circuit. In a different approach, the force exerted onto the force sensor 114 via the pulley 104 may be measured via a piezo-resistive force sensor, a pressure transducer, a thin film pressure sensor, or any other force-measuring sensor could be employed.

A spacer 118 is included to control the position of the pulley 104 relative to the force sensor 114. A printed circuit board (PCB) 120 contains the microprocessor 121 as well as peripheral integrated circuity for processing the signals received from the force sensor 114 and rotation sensor 108. Additionally, the PCB 120 includes a wireless communication device 123 (e.g., a wireless transmitter) for transmitting the data that is recorded by the sensors. The PCB also includes a wire connector 125 such as a barrel connector for providing and receiving wired data transmission, power, or both data transmission and power simultaneously.

Figure 3:
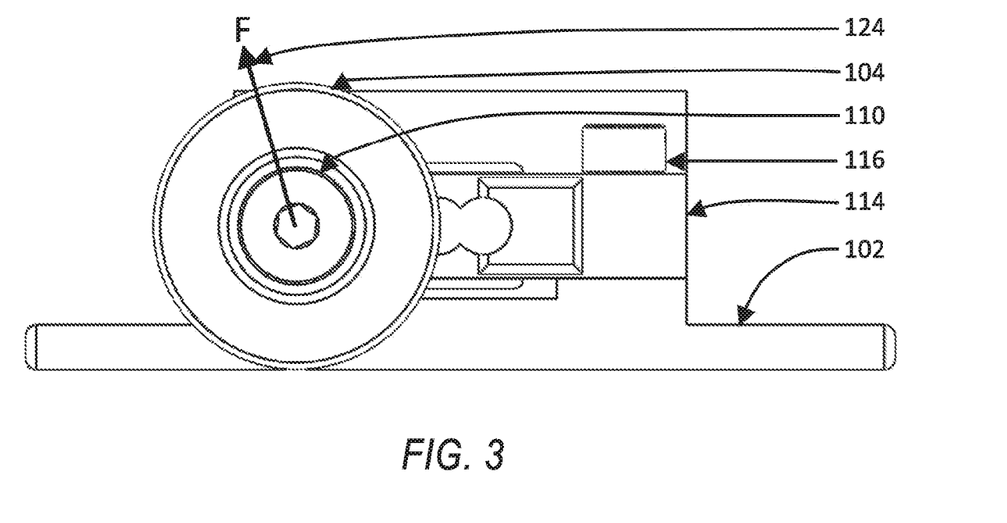
FIG. 3 shows a cross-sectional side view of the device shown in FIG. 1.

FIG. 3 shows a side view of the weight machine sensor 100 shown in FIG. 1 with the cover 106 and associated screws 122 removed. This figure more clearly illustrates how the pulley 104 is connected to a force sensor 114 which in this example configuration utilizes strain gauges applied to a beam cantilevered from the base 102. An example of the direction of force 124 is shown with an arrow, but the force sensor 114 can be configured to measure force applied in any direction. For example, if a cable is routed such that it contacts the top of the pulley 104 the direction of force will be downward, while if the cable is routed such that it contacts the bottom of the pulley 104 the direction of force will be upward.

Figure 4:
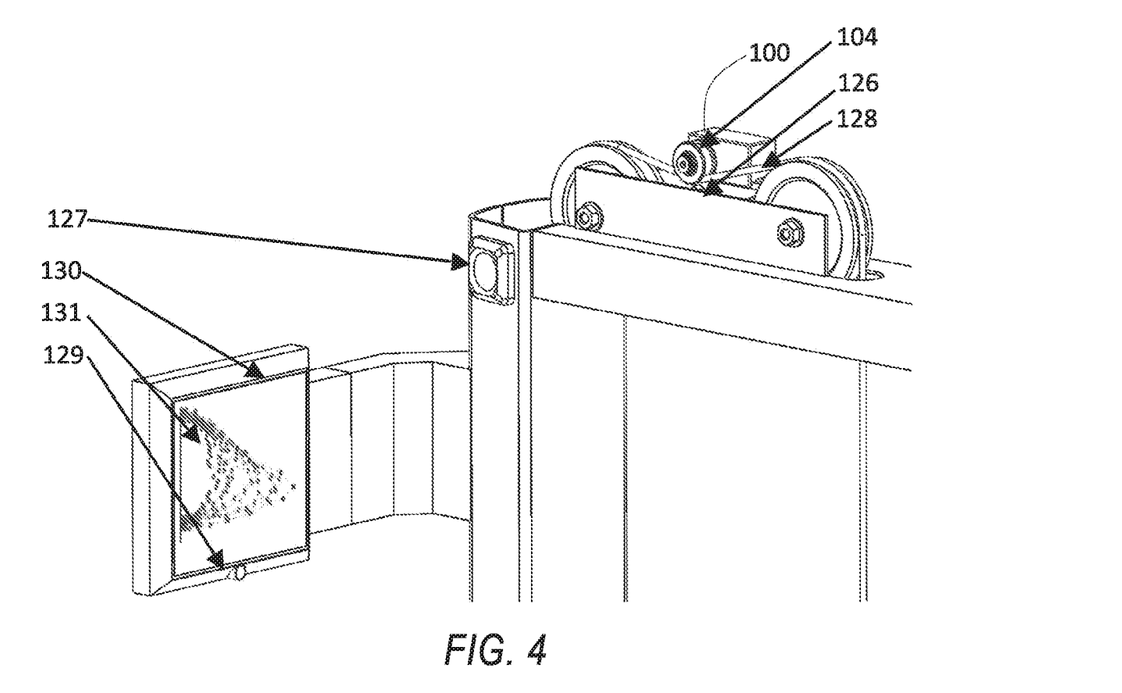
FIG. 4 shows the device in FIG. 1 incorporated into the frame of a weight machine.

FIG. 4 shows a perspective view of the weight machine sensor 100 affixed to the rigid frame 126 of the exercise machine. The sensor 100 may be associated with (e.g., identify or otherwise distinguish) the user performing the exercise. This association may facilitate workout tracking and progress monitoring over time as well as administer more sophisticated automated coaching programs which would be unique to each user. A short range communication device 127, implemented via an antenna, circuits, chips, and possibly other electronic components could be integrated into the sensor system. Examples of the short range communication device 127 may include a near field communication (NFC) or radio frequency identification (RFID) check-in electronic (hardware) module. Most fitness trackers, wearables, smart phones, and smart watches include NFC or RFID readable chips which could be used to check the user in to the exercise machine. Members of commercial gyms are also commonly issued keychain fobs, bracelets, or other ways to identify themselves when they check in to the gym that could also be used to check in to the individual exercise machine stations using the short range communication device 127. An optical camera 129 coupled with facial recognition functionality could also be used to scan the individual's face as a way to identify which user is at the machine. A retina scanners or fingerprint scanner could similarly provide the ability for the user to be identified without requiring him or her to wear or carry an NFC/RFID equipped item. A dedicated monitor 130 on the exercise machine allows real-time data and coaching feedback 131 to be displayed to the user. The data could be transmitted from the weight machine sensor 100 to the monitor wirelessly or physically wired via the wire connector 125 included on the PCB 120. The coaching feedback 131 displayed on the screen could include time-series data such as force, power, repetition count, calories burned, position, or total work output for that set. It could also include scatter plots that do not include time on one of the axes but rather a combination of two of the coaching metrics. For example, a graph showing power on one axis and position on the other axis could be useful. Or repetition count on one axis and total work on another axis as another example. But any combination of metrics provided by the sensor could be configured to suit the needs of the coaching paradigm, trainer, or exerciser. These metrics could be displayed on the dedicated monitor 130 or a remote device 190 (see FIG. 1), such as a mobile phone, smartwatch, or wearable activity tracker, or to a remote server 195 (see FIG. 1), such as a cloud-based server or a server associated with a particular facility (e.g., a gym).

A bracket may allow the base 102 to be rigidly mounted to the frame 126 such that any force transferred from the cable 128 to the pulley 104 is thereby detected by the force sensor 114. If the cable 128 were to pass by the pulley 104 without being rerouted such that it remained a straight line, there could be sufficient friction to rotate the pulley 104 and therefore record motion and position data via the rotation sensor 108. To record data regarding the amount of weight lifted, however, the tension in the cable 128 should also be measured. For this reason, the pulley 104 should actively reroute the cable 128 by some angle. The force applied by the cable 128 to the pulley 104 can then be measured by the force sensor 114 to deduce the tension in the cable and therefore the amount of resistance experienced by the user.

Figure 5:
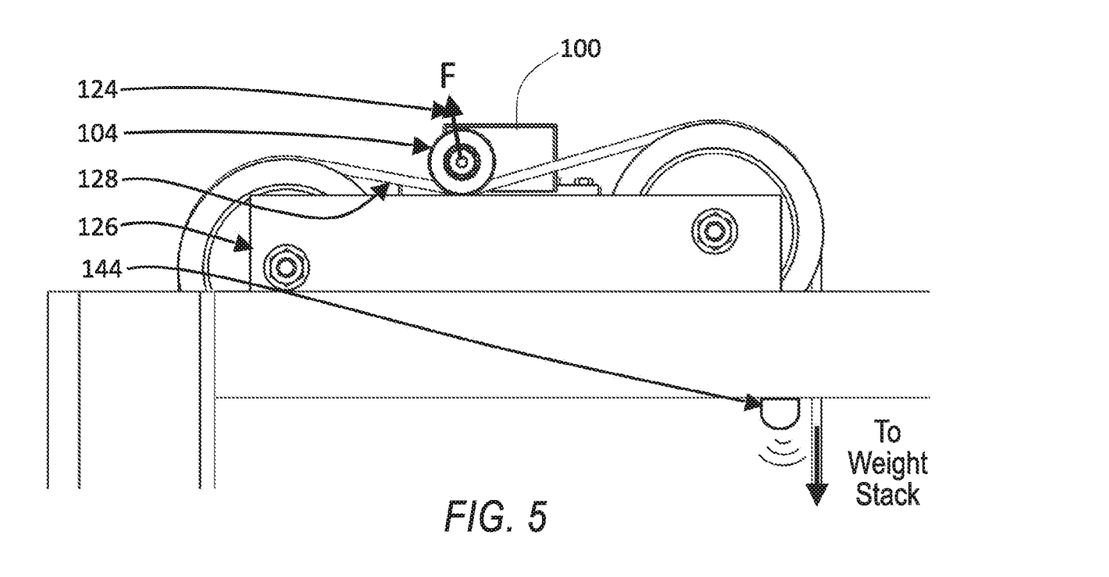
FIG. 5 shows the configuration of FIG. 4 from a side view illustrating how the tension in the cable of the weight machine translates into force exerted onto the pulley.

FIG. 5 shows a side view of the configuration shown in FIG. 4. This angle makes the resultant force 124 applied to the pulley 104 by the cable 128 more apparent. Rerouting the cable 128 by a small angle will result in a force 124 that is small relative to the tension in the cable. Rerouting the cable 128 by a large angle, conversely, will result in a relatively higher force 124. Translating the force measurement to weight values can be achieved by calibrating the device as the relationship is in most cases a basic linear fit. For the weight machine sensor to measure adequate information about the exercise being performed, it measures two basic details of the activity: the amount of weight being lifted and the motion behavior of the weight stack 134. The force sensor incorporated into the base and pulley assembly allows the sensor to deduce the weight being lifted, but there are more ways to measure the motion behavior of the weight stack 134. One configuration presented earlier features a rotation sensor on the pulley. Another approach is to use an optical position sensor 144 that is mounted to the frame 126 of the weight machine and oriented toward the weight stack 134 to measure its position. The position sensor 144 could include an infrared sensor, a lidar sensor, an ultrasonic sensor, or any other form of position detection. Mounting the position sensor 144 in a position where it is fixed relative to the sensor is most convenient, but the same results could be achieved by mounting the position sensor 144 such that it moves relative to the weight stack 134 and measures position relative to a fixed object such as the frame 126. The examples just cited feature an optical way to "watch" the behavior of the weight stack 134 without any physical interaction, but a string wrapped around a rotary encoder that extends from the weight stack 134 could also be used as a way to measure the motion behavior. Another way to deduce the weight setting used by the user would be to connect the weight selector pin to the aforementioned string. Because the weight setting selection locations typically begin with the lightest weight settings near the top of the weight stack 134 and the heaviest weight setting at the bottom, the length of the string when it is in its selector location could indicate the weight resistance chosen by the user. In this example, a single rotary encoder could be used to determine both the weight setting selected by the user and the motion behavior of the weight stack 134.

Figure 6:
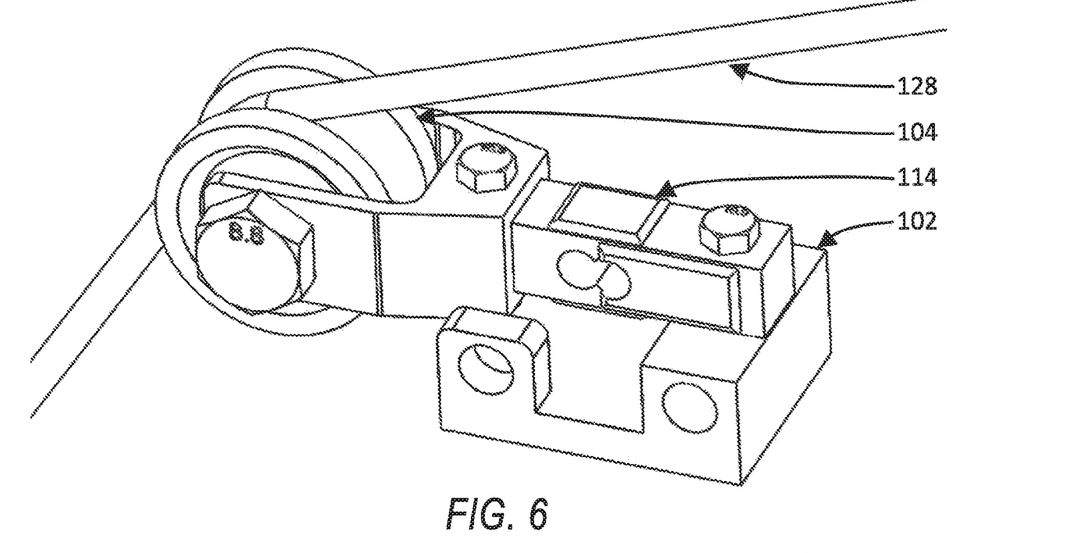
FIG. 6 shows a configuration of the weight machine sensor in which the pulley is in line with the force sensor.

FIG. 6 shows a configuration of the weight machine sensor in which the pulley 104 is in line with the force sensor 114, rather than cantilevered off the side as shown in the configuration represented in FIG. 1.

Figure 7:
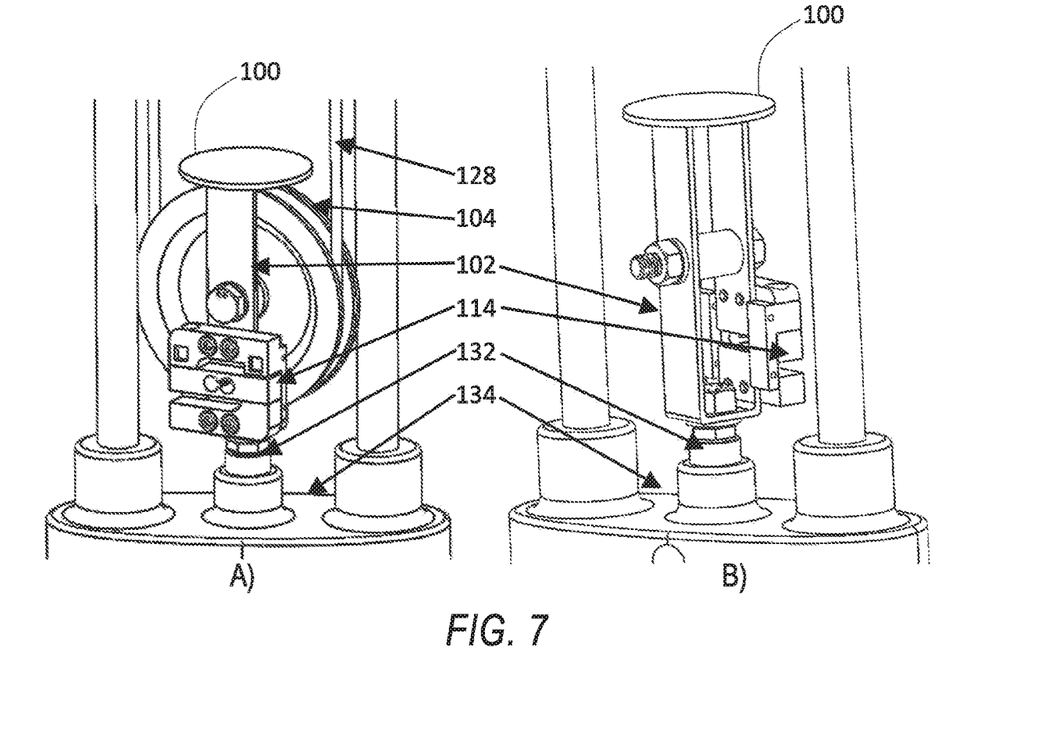
FIG. 7 shows a configuration of the weight machine sensor in which the base mounts directly to the moving stack of weights.

FIG. 7A shows a configuration of the weight machine sensor in which the base 102 has a bracket for containing the pulley 104, and the base 102 mounts directly to a weight selector tube 132 which in turn raises the stack of weights 134. In this configuration, a portion of the bracket is removed such that force exerted onto the pulley 104 by the cable 128 is transferred, at least in part, through the force sensor 114 attached to the base 102. The example shown here features an "S type" load cell as the force sensor but other configurations or force sensor types could be employed. FIG. 7B shows an alternate view of the configuration shown in FIG. 7A but with the pulley 104 and cable 128 removed to illustrate the portion of the base 102 that is removed so that the force experienced by the user from the movement of the weight stack 134 is transferred through the force sensor 114. In this example featuring just one force sensor 114, only about half of the force will be measured, but two force sensors could be used on both halves of the bracket or base 102 such that the total force applied to the pulley 104 is measured. This configuration of the weight machine sensor 100 could include a rotation sensor 108, a motion sensor, or both. Because the device is moving, an accelerometer could be used as a motion sensor, although position sensors such as infrared (IR), ultrasonic, or lidar, for example, could also be used. In some scenarios such as a multi-gym environment where multiple exercise types can be conducted at the same station, the pulley 104 might be lifted by the cable 128 on the left side causing clockwise motion, lifted by the right side causing counter-clockwise motion, or lifted by both sides simultaneously to allow for raising the weights with little or no rotation of the pulley 104. To detect exercise types and gather more data about the exercises being performed it would therefore be beneficial include both rotation data and motion data for this example application.

Figure 8:
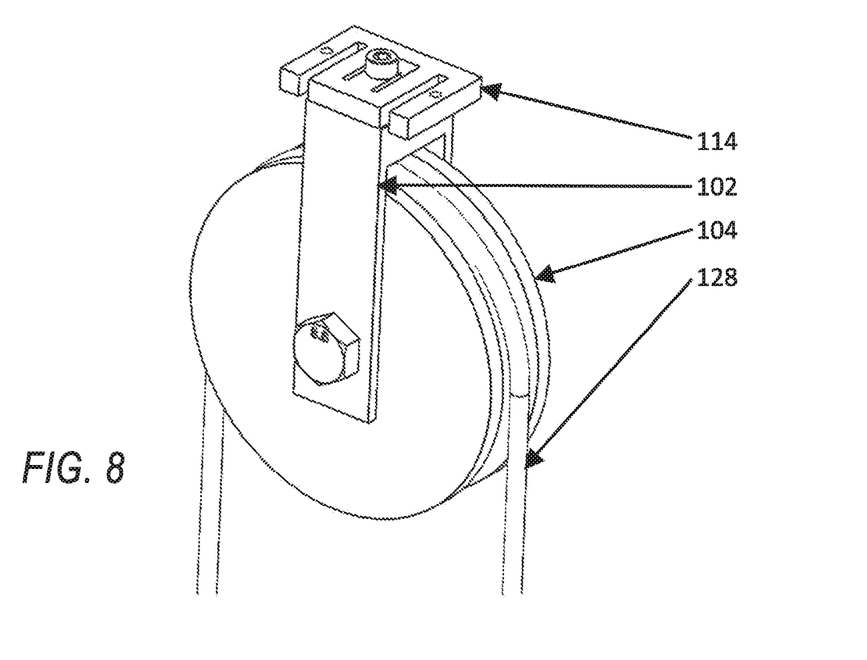
FIG. 8 shows a configuration of the weight machine sensor featuring an "E type" load cell as the force sensor.

FIG. 8 shows a configuration of the weight machine sensor featuring an "E type" load cell as the force sensor. In this sample configuration, the force sensor 114 could be positioned to measure force transferred between the base 102 and the fixed, rigid frame 126 of the weight machine. Alternatively, the force sensor 114 could be positioned to measure force transferred between the base 102 and the weight selector tube 132. In other words, the weight machine sensor 100 could be positioned such that it is stationary or it could be positioned such that it moves in accordance with movement of the weights or other resistance source.

Figure 9:
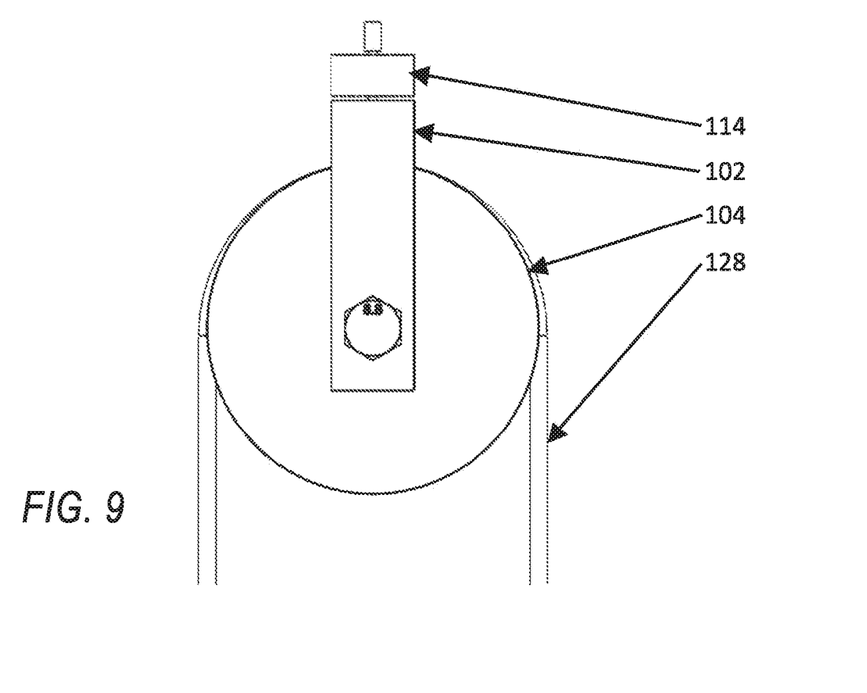
FIG. 9 shows a configuration of the weight machine sensor featuring a button type load cell as the force sensor.

FIG. 9 shows a variation of the weight machine sensor 100 shown in FIG. 8 but features a button type load cell as the force sensor rather than an "E type" load cell.

Figure 10:
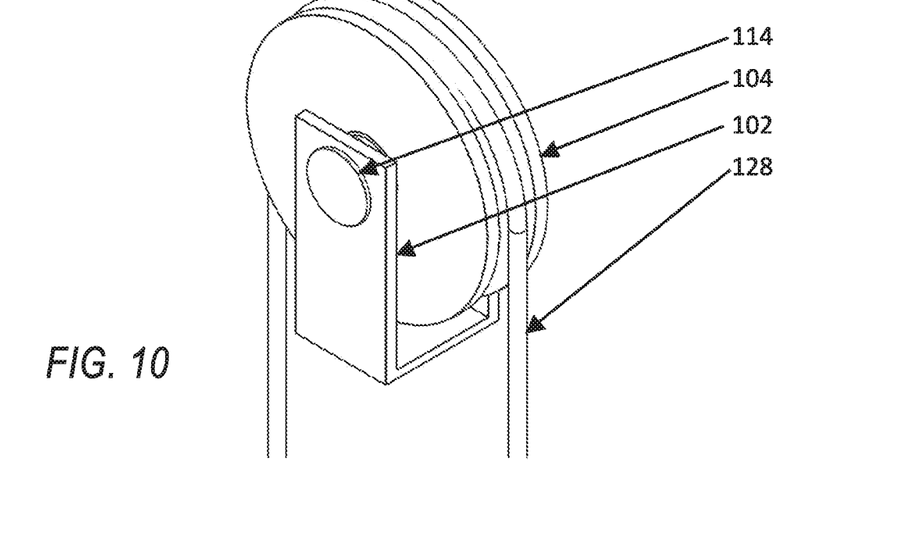
FIG. 10 shows a configuration of the weight machine sensor featuring a load pin load cell integrated into the shaft of the pulley as the force sensor.

FIG. 10 shows a configuration of the weight machine sensor 100 featuring a load pin load cell integrated into the shaft of the pulley as the force sensor 114.

Figure 11:
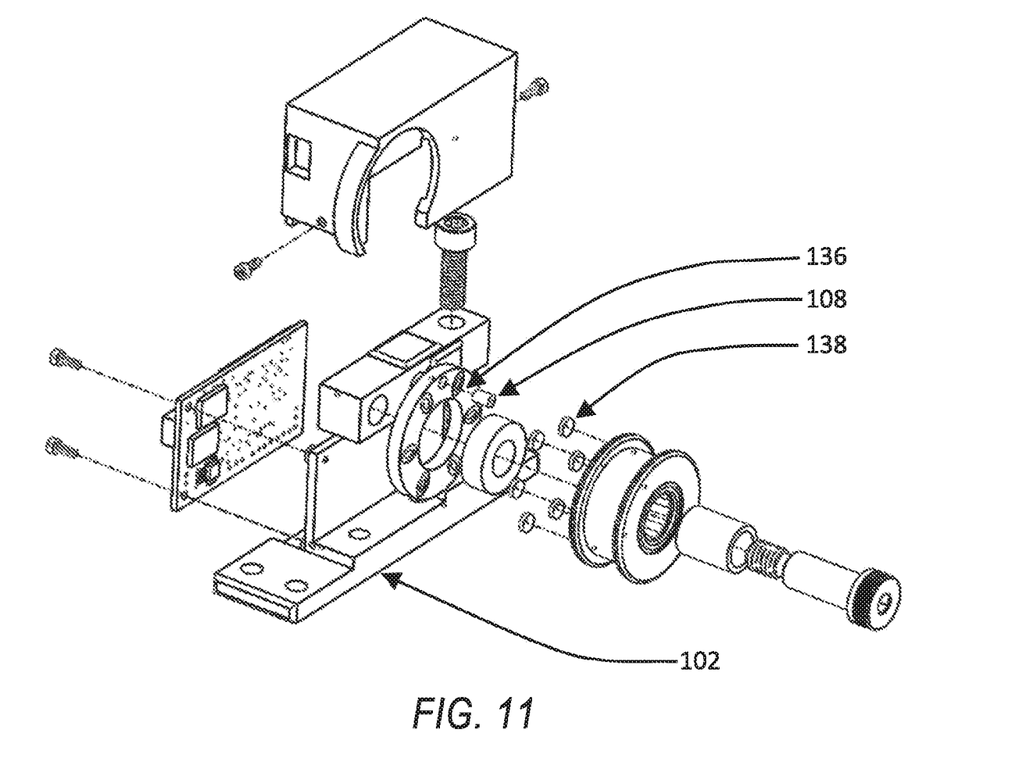
FIG. 11 shows a configuration of the weight machine sensor featuring componentry to facilitate kinetic charging of a battery.

In commercial gym environments it can be difficult or cumbersome to route power cables to the weight machines, so harvesting energy as a way to power the electronics on the PCB 120, microprocessor 120, and wireless communication device 123 would eliminate the need to plug the device in or replace batteries. FIG. 11 shows an exploded view of the same weight machine sensor 100 shown in FIG. 2, but with some additional kinetic charger components to facilitate kinetic charging of a battery that powers the device. In this sample configuration, the kinetic charger components include electrical coils 136 fixed to the base 102 and positioned in such a way that an electrical current is generated when the plurality of magnets 138 rotate. The magnets 138 are mounted in a fashion such that rotation of the pulley 104 causes rotation of the magnets 138 and therefore the production of an electrical current through the coils 136. The circuitry could be set up such that the resulting torque applied to the pulley from electromagnetic induction will be experienced only when the weights are being lowered to not add any additional resistance when the weights are being lifted. In this case, electricity would also only be generated when the weights are being lowered. One possible rotation sensor 108 technology features rotating magnets and a hall-effect or reed sensor to deduce rotational position and rotational direction data. The rotation sensor 108 could be situated such that the magnets 138 used for kinetic charging could also be used for rotation detection.

Figure 12:
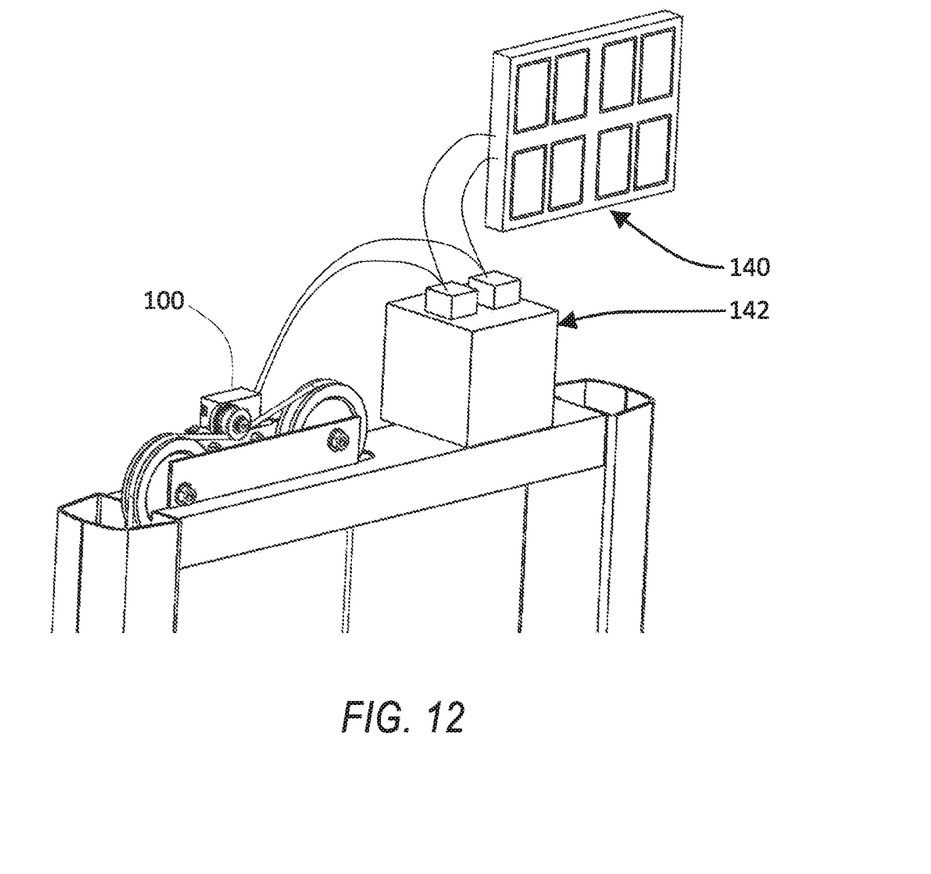
FIG. 12 shows a configuration of the weight machine sensor featuring a solar panel for charging of a battery.

FIG. 12 illustrates another possible way to harvest energy featuring a solar panel 140 to charge a battery 142 that runs the electronics on the weight machine sensor 100. Whether the gym is outdoors or indoors, the presence of some form of lighting means that a solar panel 140, or photovoltaic cell of some form, could provide the power required to run the device. The weight machine sensor 100 operates in a "low-power" or "sleep" mode for extended periods of time and will "wake up" and transmit data only when in use. A wake sensor allows for this functionality. Given these usage patterns the solar panel 140 need not be able to provide the maximum power requirement such as when the device is awake and transmitting data wirelessly, but rather merely provide the average power requirement. The presence of a battery 142 allows for a buffer to store the harvested energy to be delivered whenever the device demands. The battery would also be included in the configuration shown in FIG. 11 featuring kinetic energy harvesting and could also be included in any of the other configurations described herein.

Figure 13:
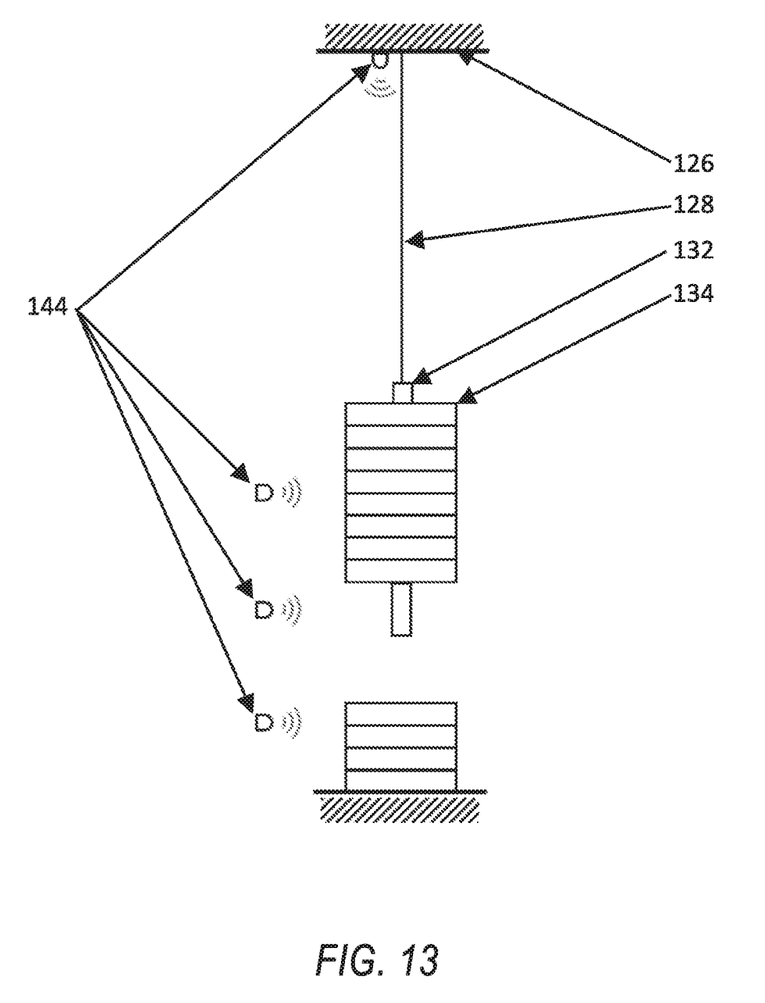
FIG. 13 shows a configuration of the weight machine sensor featuring a plurality of position sensors for detecting the weight setting on an exercise machine as well as the motion behavior of those weights during an exercise.

FIG. 13 demonstrates a configuration of the weight machine sensor 100 wherein a plurality of optical position sensors 144 can be arranged in a manner to allow detection of the amount of weight resistance chosen from the weight stack 134 as well as the motion behavior of the weight stack 134. The position sensors 144 could include an infrared sensor, a lidar sensor, an ultrasonic sensor, or any other form of position detection or combination thereof. A position sensor 144 arranged on the frame 126 of the machine facing downward, for example, could view the motion of the weight stack 134 while position sensors 144 arranged adjacent to the weight stack, possibly horizontally angled, could view the weight stack 134 from a different angle and thereby be used by the microprocessor 121 to infer the weight setting. By overlaying data from the various position sensors 144 the algorithms implemented on the microprocessor 121 could calculate the thickness of the material being moved and therefore determine the weight setting and therefore the exercise data produced by other configurations of the weight machine sensor.

The combination of the force sensor 114 and rotation sensor 108 data (or position sensor 144 data), which the microprocessor 121 is programmed to determine from the force signal output by the force sensor and the motion signal output by the rotation sensor, respectively, allows for calculation of many exercise metrics (referred to as "exercise data") that allow the exerciser to monitor the progress of his/her physical fitness and automate the delivery of coaching feedback 131. For example, the user's strength, force, power, work output, calorie expenditure, repetition count, and weight resistance settings can all be tracked and compared to historical performance. That is, the microprocessor 121 may be programmed to calculate strength, force, power, work output, calorie expenditure, and weight resistance setting from the force signal output by the force sensor, the motion signal output by the position/rotation sensor, or both. The metrics also allow for engagement with an interactive community whose members could be in close proximity or geographically dispersed. For example, the metrics could be displayed on a leaderboard with real time comparisons of the group of participants, or the participants could be exercising in a home gym environment with a similar leaderboard monitoring and comparing everyone's progress. The workouts that are part of this described experience could be self-guided, loaded on an "on-demand" basis, or streamed live onto the user's television, mobile device, or wearable fitness tracker.

The wireless communication device 123 may be implemented via an antenna, circuits, chips, or other electronic components configured or programmed to facilitate wireless communication. For instance, the wireless communication device may be programmed to transmit the data collected by the force sensor, rotation sensor, or both via a telecommunication protocol such as Bluetooth®, Bluetooth Low Energy®, etc., to a remote device 190 (see FIG. 1) such as a mobile phone, smartwatch, or wearable activity tracker, or to a remote server 195 (see FIG. 1), such as a cloud-based server or a server associated with a particular facility (e.g., a gym). Wireless communication could be the only way to communicate the exercise data or it could be secondary to data transmission via a wired connection such as with an ethernet cable. Multiple formats of wireless communication could also be used in combination to allow simultaneous streaming of data to a remote device 190 and a remote server 195, for example. The term "server" refers to a computer having a processor and memory. The term "remote" when used in the context of the remote device and remote server may refer to the spatial relationship of the remote device, the remote server, or both, relative to the exercise tracker. Therefore, although referred to as "remote," the remote device 190 and remote server 195 may be physically near the exercise tracker 100 (i.e., the remote server 195 may be in communication with the exercise tracker 100, the remote device 190, or both, via a local network connection). Alternatively, the remote device 190 or remote server 195, or both, may be physically "remote" but still in signal communication with the exercise tracker 100 (e.g., the remote server 195 may be cloud-based). Accordingly, in some implementations, the data may be transmitted from the weight machine sensor 100 to the remote device 190 or the remote server 195 (see FIG. 1) via a Wi-Fi network connection. The wireless communication device may be programmed to periodically transmit the collected data to the remote device or remote server, or transmit the data as it is collected. Alternatively, the wireless communication device may be programmed to transmit the data to the remote device or the remote server 195 at specific times, such as when all repetitions have been performed or when a workout is complete. The wireless communication device may determine that all repetitions have been performed based on the force sensor signal or that the workout is complete in response to a user input provided to the exercise machine input or remote device 195.

In general, the computing systems and/or devices described may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX, macOS, and iOS operating systems distributed by Apple Inc, of Cupertino, Calif., the BlackBerry OS distributed by Blackberry, Ltd. of Waterloo, Canada, and the Android operating system developed by Google, Inc. and the Open Handset Alliance. Examples of computing devices include, without limitation, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc.

Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The invention claimed is:

1. A weight machine sensor comprising:
   a force sensor programmed to output a force signal representing a force applied to a pulley disposed on a cable incorporated into exercise equipment having a stack of weights;
   a position sensor positioned above the stack of weights and oriented toward a top surface of the stack of weights, wherein the position sensor is programmed to measure linear motion of the stack of weights and output a position signal representing the measured linear motion; and
   a processor programmed to receive the force signal and the position signal and determine, from the force signal and the position signal, exercise data including an amount of exercise resistance and a number of repetitions performed.

2. The weight machine sensor of claim 1, further comprising a wireless communication device programmed to wirelessly transmit at least one of the force signal, the position signal, and the exercise data.

3. The weight machine sensor of claim 2, wherein the wireless communication device is programmed to wirelessly receive communications from a remote server.

4. The weight machine sensor of claim 1, wherein the processor is programmed to command the wireless communication device to transmit the exercise data to a remote device.

5. The weight machine sensor of claim 1, further comprising a battery operably connected to at least one of the force sensor, the position sensor, and the processor.

6. The weight machine sensor of claim 5, further comprising at least one of a kinetic charger and a solar panel to charge the battery.

7. The weight machine sensor of claim 1, further comprising a base fixed to the frame of the exercise equipment and supporting at least one of the force sensor, the position sensor, and the processor.

8. The weight machine sensor of claim 1, further comprising a monitor disposed on the exercise equipment, wherein the processor is programmed to output exercise metrics based on at least one of the force signal and the position signal to the monitor.

9. The weight machine sensor of claim 8, wherein the processor is programmed to output coaching metrics in real-time to the monitor.

10. The weight machine sensor of claim 8, further comprising a short range communication device, wherein the monitor is programmed to display a user identification prompt and wherein the short range communication device is programmed to output an identification signal representing a user of the exercise equipment.

11. The weight machine sensor of claim 1, further comprising a short range communication device in communication with the processor and programmed to output an identification signal representing a user of the exercise equipment.

12. The weight machine sensor of claim 11, wherein the short range communication device is programmed to detect the user based on a proximity of the user to the short range communication device.

13. The weight machine sensor of claim 1, further comprising an optical camera in communication with the processor and programmed to perform a facial recognition technique to identify a user of the exercise equipment.

14. The weight machine sensor of claim 1, wherein the processor is programmed to calculate calories burned by a user of the exercise equipment based at least in part on the force signal and the position signal.

15. The weight machine sensor of claim 1, further comprising a base fixed to a movable part of the weight stack and supporting at least one of the force sensor, the position sensor, and the processor.

16. The weight machine sensor of claim 1, wherein the force sensor includes a load pin load cell disposed on a shaft of the pulley.

17. The weight machine sensor of claim 1, wherein at least one of the force sensor, position sensor, and processor are programmed to operate in a low power mode.

18. A weight machine sensor comprising:
a force sensor programmed to output a force signal representing a force applied to a pulley disposed on a cable incorporated into exercise equipment having a stack of weights;
a position sensor positioned above the stack of weights and oriented toward a top surface of the stack of weights, wherein the position sensor is programmed to measure linear motion of the stack of weights and output a position signal representing the measured linear motion;
a processor programmed to receive the force signal and the position signal and determine, from the force signal and the position signal, exercise data including an amount of exercise resistance and a number of repetitions performed;
a wireless communication device programmed to wirelessly transmit at least one of the force signal, the position signal, and the exercise data to a remote server; and
a short range communication device in communication with the processor and programmed to output an identification signal representing a user in close proximity to the exercise equipment.

19. The weight machine sensor of claim 18, wherein the force sensor includes a load pin load cell disposed on a shaft of the pulley.

20. A weight machine sensor comprising:
a force sensor programmed to output a force signal representing a force applied to a pulley disposed on a cable incorporated into exercise equipment;
a position sensor programmed to measure linear motion and output a position signal representing the measured linear motion when the position sensor is positioned above a stack of weights and oriented toward a top surface of the stack of weights;
a processor programmed to receive the force signal and the position signal and determine, from the force signal and the position signal, exercise data including an amount of exercise resistance and a number of repetitions performed;
a base fixed to the frame of the exercise equipment and supporting at least one of the force sensor, the position sensor, and the processor;
a wireless communication device programmed to wirelessly transmit at least one of the force signal, the position signal, and the exercise data to a remote server; and
a short range communication device in communication with the processor and programmed to output an identification signal representing a user in close proximity to the exercise equipment.

* * * * *